United States Patent
AlQallawi et al.

(10) Patent No.: US 11,433,096 B2
(45) Date of Patent: Sep. 6, 2022

(54) OPHTHALMIC FORMULATION AND METHODS OF USE

(71) Applicants: Abdelhamid Muhammad AlQallawi, Alexandria (EG); Sherif Abdelhamid AlQallawi, Alexandria (EG)

(72) Inventors: Abdelhamid Muhammad AlQallawi, Alexandria (EG); Sherif Abdelhamid AlQallawi, Alexandria (EG)

( * ) Notice: Subject to any disclaimer, the term of this patent is extended or adjusted under 35 U.S.C. 154(b) by 0 days.

(21) Appl. No.: 17/371,303

(22) Filed: Jul. 9, 2021

(65) Prior Publication Data

US 2022/0008459 A1    Jan. 13, 2022

Related U.S. Application Data (60) Provisional application No. 63/049,970, filed on Jul. 9, 2020.

(51) Int. Cl.
| | |
|---|---|
| *A61K 33/30* | (2006.01) |
| *A61P 27/06* | (2006.01) |
| *A61P 27/04* | (2006.01) |
| *A61P 27/12* | (2006.01) |
| *A61K 9/00* | (2006.01) |
| *A61K 45/06* | (2006.01) |

(52) U.S. Cl.
CPC ............ *A61K 33/30* (2013.01); *A61K 9/0048* (2013.01); *A61K 45/06* (2013.01); *A61P 27/04* (2018.01); *A61P 27/06* (2018.01); *A61P 27/12* (2018.01)

(58) Field of Classification Search
CPC ........ A61K 31/315; A61K 33/70; A61P 27/06
See application file for complete search history.

(56) References Cited

FOREIGN PATENT DOCUMENTS

| | | |
|---|---|---|
| JP | 2003146892 A | 5/2003 |
| JP | 2006151828 A | 6/2006 |
| JP | 2015063509 A | 4/2015 |
| RU | 2281086 C1 | 8/2006 |

OTHER PUBLICATIONS

International Search Report and Written Opinion issued in corresponding foreign application PCT/IB2021/056171, dated Oct. 11, 2021, 11 pages.
Abdul-Hussein, B.A. et al. "Role of Topically-Applied Zinc Sulfate in Prevention of Sodium Selenite-Induced Cataract in Rabbits," International Journal of Advanced Research (2014), vol. 2, Issue 3, 1014-1022.
Álvarez-Barrios, A., et al. "Antioxidant Defenses in the Human Eye: A Focus on Metallothioneins," Antioxidants, 10(1), 89 (2021), 33 pages.
Barman, S., et al., "Zinc Supplementation Ameliorates Diabetic Cataract Through Modulation of Crystallin Proteins and Polyol Pathway in Experimental Rats," Biological Trace Element Research, 187(1), 212-223 (2018).
Beauchamp, M. H et al., "Role of thromboxane in retinal microvascular degeneration in oxygen-induced retinopathy," J Appl Physiol. 90: 2279-2288 (2001).
Heckenlively, J.R. et al., "Clinical Findings and Common Symptoms in Retinitis Pigmentosa" Am J Ophthalmol. 105 (5): 504-511 (1988).
Heruye, S. H., et al. "Current Trends in the Pharmacotherapy of Cataracts," Pharmaceuticals 13(1), 15 (2020), 41 pages.
Karcioglu, Z. A. "Zinc in the Eye" Survey of Ophthalmology, 27(2), 114-122 (1982).

*Primary Examiner* — Kevin E Weddington
(74) *Attorney, Agent, or Firm* — J. Peter Paredes; Amin Talati Wasserman LLP (57) ABSTRACT

Provided herein are methods and compositions for an eye drop and medication. Accordingly, the eye drop and medication have the potential for the provision of and pioneering non-surgical treatment of eye conditions.

14 Claims, 2 Drawing Sheets

OPHTHALMIC FORMULATION AND METHODS OF USE

CROSS-REFERENCE TO RELATED APPLICATIONS

The present application claims priority to U.S. provisional application Ser. No. 63/049,970, filed Jul. 9, 2020, herein incorporated by reference in its entirety.

BACKGROUND

The invention generally relates to therapies, and more specific to eye therapies.

According to the International Agency for the Prevention of Blindness (https://www.iapb.org/knowledge/what-is-avoidable-blindness/cataract/), The World Health Organization (WHO) estimates that nearly 18 million people are bilaterally blind from cataract in the world, representing almost half of all global cases of blindness. Cataract remains the leading cause of blindness and an important cause of visual impairment across the globe.

Until now, the only available treatment of cataract is having a surgical operation for removing the cloudy lens and replacing it with a clear artificial lens. To the best of our knowledge, the FDA has not yet approved any non-surgical pharmacological drugs (including eye drops) to prevent, deter, or cure cataract.

The present invention attempts to solve these problems, as well as others.

SUMMARY OF THE INVENTION

Provided herein are methods and compositions for an ophthalmic medication. Accordingly, the ophthalmic medication has the potential for the provision of and pioneering non-surgical treatment of eye conditions and diseases.

The methods, systems, and compositions are set forth in part in the description which follows, and in part will be obvious from the description, or can be learned by practice of the methods, compositions, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, compositions, and systems, as claimed.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of the applicant in the lineage of this application or in any other lineage or in any prior filed application of any third party are explicitly reserved. Nothing herein is to be construed as a promise.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with a detailed description of certain specific embodiments of the invention. Furthermore, embodiments of the invention may include several novel features, no single one of which is solely responsible for its desirable attributes or which is essential to practicing the invention described herein.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein is merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Definitions

As used herein, the term "therapeutically effective concentration" means an amount that will inhibit the progression or formation of cataracts in an eye or inhibit the progression or formation of ophthalmic disease. "Therapeutically effective concentrations" means an amount sufficient to achieve an expected therapeutic and/or prophylactic effect, such as an amount that results in the prevention or reduction of symptoms associated with ophthalmic disease. The amount of composition administered to a subject will depend on the type and severity of the disease and individual characteristics such as overall health, age, sex, weight, and drug resistance. This will also depend on the stage, severity and type of disease. One of ordinary skill in the art can determine the appropriate dose depending on these and other factors. The composition can also be administered in combination with one or more additional therapeutic compounds. In the methods described herein, a zinc compound and antihistamine are administered to a subject having one or more signs or symptoms of ophthalmic disease. For example, a "therapeutically effective amount" of a zinc compound and antihistamine formulation means a concentration that, at a minimum, improves the physiological effects of an ophthalmic disease or condition.

The "therapeutically effective amount" of the zinc compound and antihistamine will depend on various factors known to those of ordinary skill in the art. Such factors include, but are not limited to, the size of the eye, the number and progression of any fully developed or developing cataracts already present in the eye, and the mode of administration. The "therapeutically effective amount" will also depend on whether the pharmaceutical composition is to be administered a single time, or whether the pharmaceutical composition is to be administered periodically, over a period of time. The period time may be any number of days, weeks, months, or years. In one embodiment, the "therapeutically effective amount" of the zinc compound is to scavenge reactive oxygen species, reduced content of total and imbalanced proportion of soluble proteins, alleviate cross-linked glycation and concomitant expression of the receptor of glycated products, and downregulating polyol pathway enzymes to defer cataractogenesis, or clear protein ashes.

As used herein, the term "therapy" or "treatment" or "relief" means both therapeutic treatment and prophylactic methods or preventive measures, the purpose is to prevent the targeted disease state or disorder. It is to suppress (decrease). After receiving a therapeutically effective amount of a zinc compound and antihistamine formulation according to the methods described herein, the subject exhibits one or more reductions or disappearances of observable and/or measurable signs or symptoms of eye disease. If indicated, the subject has been successfully "treated" for eye disease. It should also be understood that the various modes of treatment or prevention of a medical condition as described are intended to mean "substantial" and include not only the whole of treatment or prevention but also the whole, including: some biologically or medically relevant results are achieved.

As used herein the term "ophthalmic composition" refers to a pharmaceutically acceptable formulation, delivery device, mechanism or system suitable for administration to the eye. The term "ophthalmic compositions" includes but is not limited to solutions, suspensions, gels, ointments, sprays, depot devices or any other type of formulation, device or mechanism suitable for short term or long term delivery of the zinc compound and antihistamine formulation to the eye. In contrast to oral formulations, for example, ophthalmic compositions exhibit specific technical characteristics associated with their application to the eyes, including the use of pharmaceutically acceptable ophthalmic vehicles that avoid inducing various reactions such as, for example, irritation of the conjunctiva and cornea, closure of the eyelids, secretion of tears and painful reactions. Specific ophthalmic compositions are advantageously in the form of ophthalmic solutions or suspensions (i.e., eye drops), ophthalmic ointments, or ophthalmic gels containing zinc compound and antihistamine formulation.

As used herein, the term "vehicle" is intended to include a carrier, diluent or excipient suitable for ophthalmic use. "Excipient" refers to an ingredient that provides one or more of bulk, imparts satisfactory processing characteristics, helps control the dissolution rate, and otherwise gives additional desirable characteristics to the compositions. In particular, the excipients are selected such that the ophthalmic composition does not trigger a secretion of tears that will entrain the active ingredient. Acceptable excipients are well known to a person skilled in the art, who will know how to select them depending on the desired formulation.

By "ophthalmic diseases" or "eye diseases" it is meant ophthalmic disorders including cataract, open-angle primary glaucoma, Acute eye floaters (Musca volitans), Acute and chronic glaucoma, Optic neuritis, Corneal Edema, Macular Edema, Optic Disc Edema, or other Edemas, Postoperative disorders, Retinal hemorrhage, retinopathy, Retinal detachment (especially for diabetic patients), Acute and chronic conjunctivitis and lacrimation, other corneal disorders, presbyopia, computer vision syndrome, eye strain, ocular inflammation, cloudy or blurred vision, dry eye syndrome, retinal diseases, vitreous opacities and lesions, pus, blocked tear duct, eye twitching, complications of diabetes mellitus and other systemic or genetic diseases affecting the eye.

As used herein, a cataract is an opacity of the crystalline lens of the eye caused by altered protein interactions in the lens. Protein interactions include misfolding of proteins as well as protein-protein interactions such as aggregation. Presbyopia is the impairment of vision due to advancing years or old age. Symptoms of presbyopia include decreased focusing ability for near objects, eyestrain, difficulty reading fine print, fatigue while reading or looking at an illuminated screen, difficulty seeing clearly up close, less contrast when reading print, need for brighter and more direct light for reading, needing to hold reading material further away in order to see it clearly, and headaches, especially headaches when using near vision. Individuals suffering from presbyopia may have normal vision, but the ability to focus on near objects is at least partially lost over time, and those individuals come to need glasses for tasks requiring near vision, such as reading. Presbyopia affects almost all individuals over the age of 40 to a greater or lesser degree. Cataracts included are all types and degrees (such as NI, NII, NIII, NIV, and Mature Cataract), including acute and chronic cases.

"Zinc compound" means any zinc sulfate, zinc sulfate heptahydrate; zinc sulfate hexahydrate; zinc dichloride; zinc pyrithione; zinc dibutyldithiocarbamate; zinc oxide; zinc acetate; zinc salicylate; zinc salts of all isomers of tocopherol hemisuccnic acid; zinc salts of straight, branched, saturated, and unsaturated chain C2 to C20 aliphatic carboxylic acids; zinc pyruvate; zinc lactate; zinc ester complexes; and zinc acetoacetonate or zinc acetoacetic ester complexes; and their N-acetylated and acyl-derivative compounds. These compounds can be prepared by procedures well known to those of ordinary skill in the art.

"Antihistamine" describes a class of drug that opposes the activity of histamine receptors in the body. In this sense of the word, antihistamines are subclassified according to the histamine receptor that they act upon. The two largest classes of antihistamines are H1-antihistamines and H2-antihistamines. H1-antihistamines work by binding to histamine H1 receptors in mast cells, smooth muscle, and endothelium in the body as well as in the tuberomammillary nucleus in the brain. Antihistamines that target the histamine H1-receptor are used to treat allergic reactions in the nose (e.g., itching, runny nose, and sneezing). In addition, they may be used to treat insomnia, motion sickness, or vertigo caused by problems with the inner ear. H2-antihistamines bind to histamine H2 receptors in the upper gastrointestinal tract, primarily in the stomach. Antihistamines that target the histamine H2-receptor are used to treat gastric acid conditions (e.g., peptic ulcers and acid reflux). Antihistamines may include brompheniramine, chlorpheniramine, dexbrompheniramine, dexchlorpheniramine, carbinoxamine, clemastine, diphenhydrarmine, pyrilamine, tripelennamine, tripolidine, methdilazine, bromodiphenhydramine, promethazine, azatadine, cyproheptadine, diphenylpyraline, doxylamine, trimeprazine, phenindamine, and hydroxyzine; or antihistamines may include evocetrizine dihydrochloride, fexofenadine, loratadine, descarboethoxyloratadine, norastemizole, desmethylastemizole, cetirizine, acrivastine, ketotifen, temelastine, ebastine, epinastine, mizolastine, and setastine. Pharmacologically acceptable salts of the antihistamine and its derivatives may be any pharmacologically compatible inorganic and organic salts thereof. Again, one of ordinary skill in the art can prepare such salts using well-known procedures.

General

The present inventive subject matter is generally directed towards ophthalmic formulations comprising a therapeutically effective amount of a zinc compound and at least one antihistamine, in therapeutically effective concentrations for the treatment and prevention of ophthalmic diseases. More preferably, the ophthalmic formulations are produced in therapeutically effective concentrations for the treatment or prevention of a sign or symptom related to cataracts.

The therapeutic effect of the active zinc compound and the antihistamine is a synergistic effect. For example, it is contemplated that a combination of the zinc compound at an active concentration can be at least 0.01%, at least 0.10%, at least 0.25%, at least 0.50%, or even at least 1.00% or more in combination with the antihistamine at an active concentration at least 0.001%, at least 0.01%, at least 0.1%, or even at least 1.00% to be effective to treating or preventing a sign or symptom associated with cataracts or eye diseases than the combined total effect of the zinc and antihistamine ingredients used separately. It should also be appreciated that a synergistic effect could arise when two or more active ingredients are combined at varied concentrations and with different zinc compounds, different antihistamines and combinations thereof (e.g., a zinc derivative and an H1 antihistamine and a H2 antihistamine). In one embodiment, using the zinc compound individually would result in a very uncomfortable feeling to the eye, so adding the antihistamine makes it a comfortable experience for the patient and allows the patient to avoid the negative irritating side effect of zinc.

The present invention provides for eye drop formulations for topical administrations of beneficial, active agents of zinc compounds and antihistamines to the eye. Topical eye drops are directed generally to therapies for the anterior segments of the eye, which are the contemplated therapies for the formulations of this invention. The anterior segment includes the anterior chamber, iris, ciliary body, lens, and the eye surface. The eye surface is composed of the cornea, conjunctiva, eyelids, lacrimal and meibomian glands, and the interconnecting nerves. The topical eye drop formulations providing release of zinc compounds and antihistamines for periods of time over days without interfering with vision.

The present invention relates to novel ophthalmic formulations suitable for administration to the eye. In various aspects of the invention these formulations are liquids, gels, ointments, or emulsified micelles (oil in water or water in oil). The formulations include at least one active zinc compound and antihistamine compound which is delivered in an ophthalmic formulation. The ophthalmic formulations of the present invention deliver therapeutic and non-toxic levels of active agents over a period of time or over a period of treatments. These formulations are both biocompatible and effectively delivering therapeutically effective amounts of the zinc compound and the antihistamine.

The therapeutically effective amount of the zinc compound and the antihistamine could be present in an eye drop, ocular inserts or other ophthalmic formulation in any suitable amount, including for example, about 0.00001%, about 0.001%, at least 0.01%, at least 0.05%, between 0.01-0.05%, at least 0.1%, at least 0.2%, between 0-0.2%, at least 0.25%, between 0.00001-0.25%, at least 0.3%, at least 0.4%, at least 0.5%, between 0.3-0.5%, at least 1%, between 0-1%, at least 0.29%, between 0.0-0.29%, between 0.1-0.3%, at least 0.35%, at least 0.45%, between 0.1-0.5%, at least 1%, between 0.5-1.0%, at least 0.75%, between 0.15-0.75%, at least 0.50%, between 0.25-0.50%, between 0.50-0.60%, or even 0.90% or more. In general and unless the context dictates otherwise, all concentrations herein should be interpreted as follows: (1) wt/wt % for solid ingredients; (2) wt/vol % for a solid in a liquid; and (3) vol/vol % for liquid ingredients. Such concentrations could advantageously be effective to prevent or relieve at least one sign or symptom associated with at least one of the following eye disorders: (a) cataracts (e.g., cloudy or blurred vision, decrease in visual acuity, sensitivity to light or glare, decreased contrast sensitivity, poor night vision, dimming, altered color vision, grey or white pupil, etc.); (b) diabetic retinopathy (e.g., blurred vision, loss of vision, macular edema, floaters, retinal and vitreous hemorrhages, exudates, etc.); (c) glaucoma (e.g., blurred vision and decreased visual acuity, loss of peripheral vision, visual field defect, optic nerve damage, high inter ocular pressure (IOP), retinal fiber defect, etc.); (d) macular degeneration (e.g., blurred vision, decreased visual acuity, distortion of straight lines, distortion in central vision, macular edema, macular drusen, maculopathy, etc.); (e) dry eye syndrome (e.g., irritated eyes, sandy or gritty sensation, red eyes, burning sensation, poor visual acuity, poor tear quality, decreased tear breakup time, poor Schirmer test performance, increased eye sensitivity to wind and heat, etc.); (f) proptosis (e.g., dryness, eye pain, eye redness, etc.); (g) keratoconus (e.g., distorted vision, ghost images, sensitivity to light, eye strain, etc.); (h) pterygium/pinguecula (e.g., distorted vision, blurred vision, decreased visual acuity, inflammation, irregular astigmatism, etc.); (i) ocular allergy (e.g., eye irritation, blurred vision, decreased visual acuity, etc.; or any other eye disorders and signs or symptoms.

Zinc and Oxidative Stress

The zinc compound, and more particularly, Zinc Sulfate acts as an important astringent that dissolves oxidized proteins, so it is very useful in dissolving cataract in all types and development degrees (such as NI, NII, NIII, NIV, and Mature Cataract) including acute and chronic cases. The use of Zinc Sulfate results in preventing or reducing the progression of cataract formation, or reversing formed cataract at different stages of its development and improving the clarity of vision and lens transparency significantly for patients, particularly for elder populations who exhibit cataract as a result of aging.

Alvarez-Barrios et al. (2021) discussed that "Oxidative stress affects all structures of the human eye with special emphasis on the ocular surface, the lens, the retina and its retinal pigment epithelium, which are considered natural barriers of antioxidant protection, contributing to the onset and/or progression of eye diseases" (p.1). As there is a clear role for oxidative stress in the onset and progression of cataractogenesis, the antioxidant properties of the zinc compound, and more particularly, Zinc Sulfate, allows it to scavenge reactive oxygen species resulting in protecting the lens. In a recent study by Barman and Srinivasan (2019), they report that "Supplemental zinc alleviated the progression and maturation of diabetes-induced cataract. Zinc was also effective in preventing the reduced content of total and imbalanced proportion of soluble proteins in the lens.

Supplemental zinc also alleviated cross-linked glycation and concomitant expression of the receptor of glycated products and oxidative stress indicators in the eye lens. Zinc supplementation further induced the concentration of heat shock protein in the eye lens of diabetic rats, specifically α-crystallin. Zinc supplementation counteracted the elevated activity and expression of polyol pathway enzymes and molecules in the lens. The results of this animal study endorsed the advantage of zinc supplementation in exerting the antiglycating influence and downregulating polyol pathway enzymes to defer cataractogenesis in diabetic rats" (p.212).

Specifically, Zinc Sulfate was suggested to retard opacities progression and lowering the opacity score (Abdul-Hussein & Alzubaidy, 2014).

In one embodiment, the therapeutically effective amount of the zinc compound and antihistamine is used as a post-operative agent to remove side effects and unpleasant disorders after eye cataract surgery by dissolving protein ashes and clears the new implanted lenses. The therapeutically effective amount of the zinc compound and antihistamine can also provide post-operative support after cornea transplant surgeries, where the eye may reject newly transplanted cornea.

The therapeutically effective amount of the zinc compound and antihistamine clarifies Corneal Edema which happens after Lasik surgeries (due to long operation duration). Epithelium gets damaged and it allows for Edema to happen, which leads to deterioration in Corneal clarity.

The therapeutically effective amount of the zinc compound and antihistamine also acts as an important ocular astringent that precipitates the sticky mucus buildup in the eye, often associated with exposure to airborne allergens, which helps clear the mucus from the outer surface of the eye.

The therapeutically effective amount of the zinc compound and antihistamine dissolves acute eye floaters (Musca volitans).

This therapeutically effective amount of the zinc compound and antihistamine in high concentration reduces eye pressure, so it is used in the treatment of acute and chronic glaucoma.

The therapeutically effective amount of the zinc compound and antihistamine treats optic neuritis (activates optic nerve).

The therapeutically effective amount of the zinc compound and antihistamine stops any kind of Edema, Macular Edema, Optic Disc Edema.

The therapeutically effective amount of the zinc compound and antihistamine treats retinal hemorrhage, neovascularization, and diabetic retinopathy.

The therapeutically effective amount of the zinc compound and antihistamine treats retinal detachment, especially for diabetic patients or emergency cases.

The therapeutically effective amount of the zinc compound and antihistamine contains a potent antihistamine (e.g. Chlorpheniramine Maleate), so it is used for the symptomatic relief of allergic conditions including conjunctivitis and it is of great value in the treatment of allergic manifestations of the eye.

The therapeutically effective amount of the zinc compound and antihistamine can be used as a lubricant and as an antiseptic.

Dosage and Administration:

Dosage and dosage regimen will depend on the nature of the particular therapeutically effective amount of the zinc compound and antihistamine used, such as the extent of the subject's eye disease, its therapeutic index, etc., the subject, and the subject's medical history. A wide range of dosage formulations for humans may be used for the therapeutically effective amount of the zinc compound and antihistamine. The dose of the compound suitably falls within a wide range of concentrations, including ED50 that is less toxic. The dose may vary within this range depending on the dosage form employed and the route of administration utilized. For any compound used in the method, a therapeutically effective dose can be estimated.

Typically, a therapeutic effective amount of the zinc compound and antihistamine is sufficient to achieve a therapeutic or prophylactic effect ranges from about 0.15 mg per zinc sulfate to about 1.2 mg of zinc sulfate per day, and about 0.03 mg to about 24 mg of chlorpheniramine maleate per day. In another embodiment, the therapeutic or prophylactic effect ranges are from about 0.000001 mg/kg body weight/day to about 10,000 mg/kg body weight/day. Preferably, the dose range is from about 0.00001 mg/kg body weight/day to about 1 mg/kg body weight/day. For example, the dose may be in the range of 1 mg/kg body weight or 10 mg/kg body weight every 2 days, or every 3 days, or 1-10 mg/kg body weight every week, every 2 weeks, or every 3 weeks. In one embodiment, a single dose of a therapeutic effective amount of the zinc compound and antihistamine ranges from 0.01 to 10,000 μg/kg body weight. In one embodiment, the concentration of a therapeutic effective amount of the zinc compound and antihistamine in the carrier ranges from 0.2 to 20,000 μg/(1 mL of formulation to be delivered). An exemplary therapeutic dosing regimen requires administration once a day, twice a day, three times a day, or four times a day. By measuring the subject's blood glucose or insulin levels and adjusting the dose or administration accordingly, the interval may be more irregular than indicated depending on the patients' symptoms. In therapeutic applications, relatively high doses are used at relatively short intervals until the progression of the disease is suppressed or stopped, preferably until the subject exhibits partial or total improvement in disease symptoms.

Thereafter, the patient can be given a prophylactic regime.

In some embodiments, a therapeutically effective amount of the zinc compound and antihistamine can be defined as the concentration of the zinc compound and antihistamine at the target tissue of 10-11 to 10-6 mol, such as about 10-7 mol. This concentration may be delivered at a systemic dose of 0.001-100 mg/kg or an equivalent dose at body surface area.

Dosage schedules will be optimized to maintain therapeutic concentrations in the target tissue, most preferably daily or weekly, but continuous (e.g., intravenous infusion or transdermal application).

In some embodiments, the dose of the therapeutically effective amount of the zinc compound and antihistamine is defined at a "low", "medium", or "high" dose level. In one embodiment, the low dose is about 0.0001 to about 0.5 mg/kg/h, preferably about 0.01 to about 0.1 mg/kg/h. In one embodiment, the medium dose is about 0.1 to about 1.0 mg/kg/h, preferably about 0.1 to about 0.5 mg/kg/h. In one embodiment, the high dose is about 0.5 to about 10 mg/kg/h, preferably about 0.5 to about 2 mg/kg/h.

Those of ordinary skill in the art may understand that the particular severity, including but not limited to the severity of the disease or disorder, the overall health and/or age of the subject, and the presence of other diseases can affect the dose and timing required for effective treatment.

Further, treatment of a subject using a therapeutically effective amount of the therapeutic composition described herein includes a single treatment or a series of treatments.

In one embodiment, the dosage is 2 drops in the affected eye(s) up to 4 times daily. In one embodiment, the maximum amount administered is 2 drops/4 times/day. The drop volume is equal to 0.05 ml on average, where $ZnSO_4$ is at a 0.30% concentration and available in the amount of about 0.15 mg per drop. Additionally, the 0.06% chlorpheniramine maleate is equal to about 0.03 mg of chlorpheniramine maleate per drop. The current maximum amount advised is 8 drops per day, which is equal to about 1.2 mg of zinc sulfate per day, and about 0.24 mg of chlorpheniramine maleate per day. In another embodiment, the amount may be 1 drop/4 times.

Figure 1:
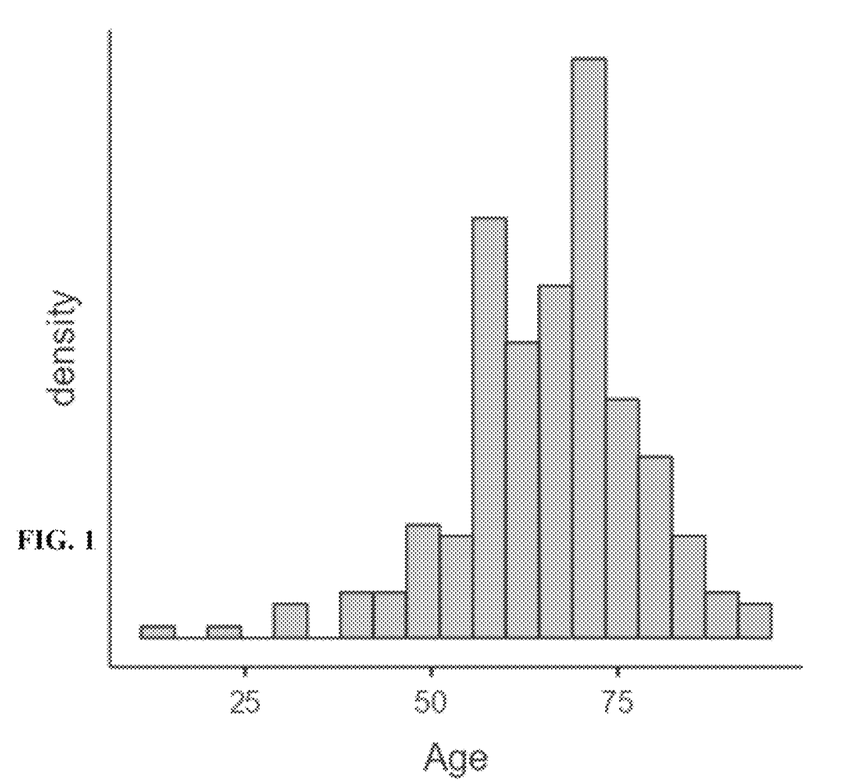
FIG. 1 is a graph showing the age of the patients who used the ophthalmic formulation according to one embodiment.
Figure 2:
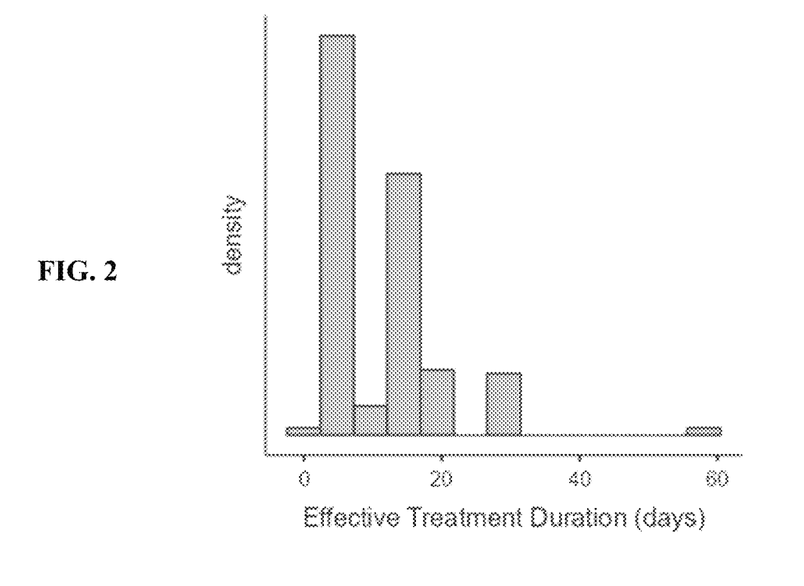
FIG. 2 is a graph showing the effective treatment duration using the ophthalmic formulation according to one embodiment.
Figure 3:
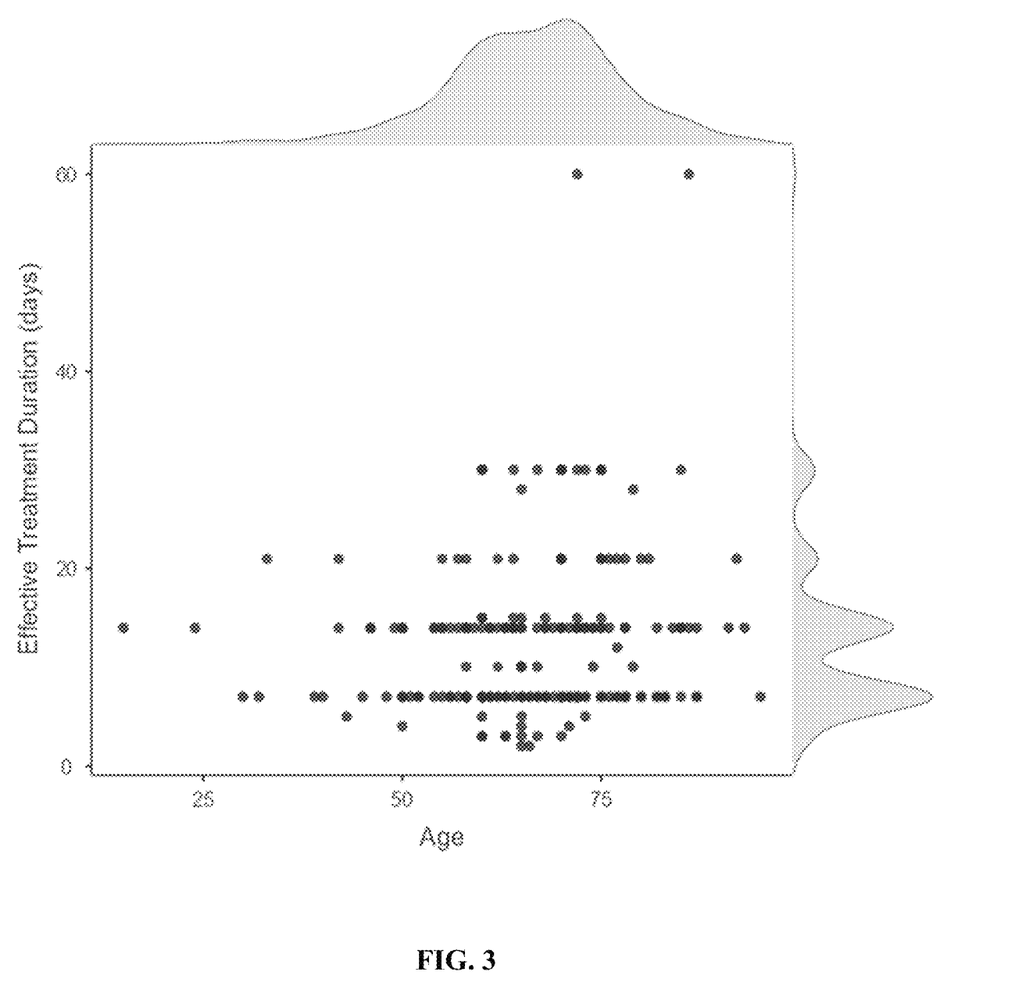
FIG. 3 is a graph showing the Effective treatment by age using the ophthalmic formulation according to one embodiment.

Example:

The eye drops were offered to 230 volunteers who were patients with diagnosed eye diseases or conditions with a focus on Cataract. Their diagnosis has been mainly done at ophthalmology clinics and eye vision centers before starting to use the eye drops. Almost 207 (about 90% of patients) have all shown positive results for the issues addressed by this eye drops formula within treatment durations ranging from 2 to 60 days in cases of cataract, and from 7 to 60 days for the other addressed cases. Participants included 108 females (47%) and 122 males (53%) with ages ranging from 15 to 95 (Mean=66.1, Standard Deviation=11.8, Median=67). The age of the patients is shown in FIG. 1. Participants included patients with other complications such as diabetes (28.3%), hypertension (17.8%), and renal (.9%) and heart failures (8.7%). Treatment results reported in the dataset are informed by either a doctor, or self-reported by the patient in cases where data obtained from the doctor's examination were not available. The effective treatment duration is shown in Table 1 and FIG. 2. FIG. 2 shows that for the effective treatment duration, there was Mean: 12.4, Median: 10, Standard Deviation: 8.2, Minimum: 2, Maximum: 60. If the 2 cases in the dataset whose condition improved in 60 days were considered as outliers, the range will be from 2 to 30. After 1 week: 41.9% showed effective treatment. After 2 weeks: 28.4% showed effective treatment. After 3 weeks: 7.9% showed effective treatment. A graph of effective treatment by age is shown in FIG. 3.

TABLE 1

| Frequencies of Effective Treatment Duration (days) | | | |
|---|---|---|---|
| Levels | Counts | % of Total | Cumulative % |
| 2 | 2 | 0.9% | 0.9% |
| 3 | 7 | 3.1% | 3.9% |
| 4 | 3 | 1.3% | 5.2% |
| 5 | 4 | 1.7% | 7.0% |
| 7 | 96 | 41.9% | 48.9% |
| 10 | 7 | 3.1% | 52.0% |
| 12 | 1 | 0.4% | 52.4% |
| 14 | 65 | 28.4% | 28.4% |
| 15 | 7 | 3.1% | 83.8% |
| 21 | 18 | 7.9% | 91.7% |
| 28 | 2 | 0.9% | 92.6% |
| 30 | 15 | 6.6% | 99.1% |
| 60 | 2 | 0.9% | 100.0% |

For Cataract there were 171 volunteers (including 44 diabetic volunteers). NI: 4 volunteers; NII: 56 volunteers; NIII: 96 volunteers; Mature: 57 volunteers. 11 cases reported partial or ineffective results (93.6% estimated effectiveness). In some cases, elderly patient volunteers were informed by their doctor that they can't go through operations due to their medical conditions, and the developed eye drops provided them with a safe alternative leading to positive treatment results.

Post-operative disorder there were 34 volunteers. 4 cases reported partial or ineffective results (88.2% estimated effectiveness). The eye drops helps as a post-operative agent to address potential surgical complications/side effects.

For Blindness there were 30 volunteers. 7 cases reported partial or ineffective results (76.7% estimated effectiveness). Multiple volunteers reported that their vision was restored gradually after using the eye drops.

For Glaucoma there were 20 volunteers. 4 cases reported partial or ineffective results (80% estimated effectiveness). The astringent properties of zinc have an important role in reducing eye pressure, so it has potential effectiveness in the treatment of acute and chronic glaucoma.

TABLE 2

| Disease/Disorder | Number of Volunteers | Number of Cases with Partial or Ineffective Treatment | Estimated Effectiveness |
|---|---|---|---|
| Cloudy/Blurred Vision | 23 | 0 | 100% |
| Floaters | 18 | 0 | 100% |
| Edema | 18 | 5 | 72.2% |
| Retinal Hemorrhage | 17 | 4 | 76.5% |
| Optic Neuritis | 14 | 5 | 64.3% |
| Conjunctivitis | 12 | 2 | 83.3% |
| Lacrimation | 11 | 2 | 81.8% |
| Retinal Detachment | 10 | 4 | 60% |
| Pus | 2 | 0 | 100% |

In one embodiment, the main active ingredient of the ophthalmic formulation is Zinc Sulfate, which can also be used as an astringent for helping reduce redness and irritation. This embodiment of Zinc Sulfate for the treatment of cataract can take place in the form of preventing or reducing the progression of cataract formation, or reversing formed cataract at different stages of its development and improving the clarity of vision and lens transparency significantly for patients, particularly for elder populations who exhibit cataract as a result of aging.

In one embodiment, the main active ingredient is Zinc Sulfate ($ZnSO_4$). In one embodiment, the concentration of zinc sulfate is about 0.30%, however higher than 0.30% or lower than 0.30% (e.g., .25%) can be used. In one embodiment, the ophthalmic composition of the formula: Zinc Sulfate at about 300 mg (0.30%), Chlorpheniramine Maleate at about 60 mg (0.06%), and in an Isotonic Buffered Solution to about 100 ml.

In another embodiment, Chlorpheniramine Maleate can be substituted with an antihistamine while maintaining synergistic treatment effectiveness.

Also, other alternative embodiment, the therapeutically effective zinc compound and antihistamine may include: Zinc Sulfate at about 250 mg, Naphazoline Hydrochloride at about 100 mg, Diphenhydramine Hydrochloride at about 125 mg, in an Isotonic Buffered Solution to about 100 ml. Although this embodiment may be effective for cataract conditions, it is contraindicated in patients with closed-angle glaucoma because of the presence of Naphazoline, which causes vasoconstriction of conjunctival blood vessels and may exacerbate the effects of glaucoma.

Also, other therapeutically effective zinc compound and antihistamine formulations may include: Zinc Sulfate at about 280 mg, Tetrahydrozoline Hydrochloride at about 50 mg, in an Isotonic Buffered Solution to about 100 ml.

Also, other alternatives therapeutically effective zinc compound and antihistamine formulations may include: Zinc Sulfate at about 290 mg, Pheniramine Maleate at about 30 mg, in an Isotonic Buffered Solution to about 100 ml.

Method of Making

For ophthalmic use, the zinc compound and antihistamine formulation is formulated into solutions, suspensions, and ointments suitable for ophthalmic use. For eye drop formulations, see generally the following references: Mitra (ed.), Ophthalmic Drug Delivery Systems, Marcel Dekker, Inc., New York, N.Y. (1993) or see the following references: Havener, W. et al., Ocular Pharmacology, C. V. Mosby Co., St. Louis (1983). Eye drops may be suitable for topical administration to the eye in the form of solutions, suspensions, ointments, creams, or solid inserts. In the case of a single administration, 0.1 ng to 5000 μg to 500 or 10 ng to 500 μg of the zinc compound and antihistamine formulation can be instilled into the human eye.

In one embodiment, zinc sulfate eye drops are a sterile solution containing 0.25% w/v of Zinc Sulfate Heptahydrate ($ZnSO_4$, $7H_2O$ in purified water. To 5 mL add 50 mL of water and 5 mL of ammonia buffer pH 10.9 and titrate with 0.01M disodium edetate VS using mordant black 11 solution as indicator. Each mL of 0.01M disodium edetate VS is equivalent to 2.875 mg of $ZnSO_4$, $7H_2O$, to provide a content of zinc sulfate heptahydrate, $ZnSO_4$, $7H_2O$, 0.22 to 0.28% w/v.

In another embodiment, the zinc sulfate eye drops include between about 0.27 w/v % and about 0.33w/v % of zinc sulfate hydrate ($ZnSO_4$, $7H_2O$: 287.55) by preparing 3 g of zinc sulfate hydrate, 20 g of Boric Acid, 5 g of sodium chloride, 2 mL of fennel oil, and sufficient quantity of purified water in a container to make 1000 mL. Prepare under ophthalmic liquids and solutions with the ingredients and pipet accurately 25 mL of zinc sulfate ophthalmic solution and add 100 mL of water and 2 mL of ammonia and titrate.

In one embodiment, preparation of zinc sulfate (0.25% w/v) eye drop (with pH 7.2±2): Zinc sulfate powder (250 mg) and 20 mg of benzalkonium chloride were dissolved in 100 ml of buffer solution (which was already consisted of 440 mg of phosphate powder in 100 ml distilled water).

Useful buffers include, but are not limited to borate buffers, phosphate buffers, carbonate buffers, acetate buffers and the like. The concentration of buffer in the ophthalmic compositions may vary from about 1 mM to about 150 mM or more, depending on the particular buffer chosen.

Depending upon the particular form selected, the compositions may contain various additives such as buffering agents, isotonizing agents, solubilizers, preservatives, viscosity-increasing agents, chelating agents, antioxidizing agents, antibacterial agents, and pH regulators.

Ophthalmic preparations may contain non-toxic substances such as antibacterial agents that are not harmful to use, such as thimerosal, benzalkonium chloride, methyl and propylparaben, benzyldodecinium bromide, benzyl alcohol, Or phenylethanol; buffer components such as sodium chloride, sodium borate, sodium acetate, sodium citrate, or gluconate: sorbitan lauric acid monoester, triethanolamine, polyoxyethylene sorbitan monopalmitate, ethylenediaminetetraacetic acid, etc. Other conventional components or preservatives may be added.

Examples of suitable preservatives include, but are not limited to chlorobutanol, sodium dehydroacetate, benzalkonium chloride, cetyl pyridinium chloride, phenethyl alcohol, parahydroxybenzoic acid esters, benzethonium chloride, hydrophilic dehalogenated copolymers of ethylene oxide and dimethyl ethylene-imine, mixtures thereof, and the like. The viscosity-increasing agents may be selected, for example, from methylcellulose, hydroxyethylcellulose, carboxymethylcellulose, hydroxypropylmethylcellulose, polyvinyl alcohol, carboxymethylcellulose, chondroitin sulfate, and salts thereof. Suitable solubilizers include, but are not limited to, polyoxyethylene hydrogenated castor oil, polyethylene glycol, polysorbate 80, and polyoxyethylene monostearate. Typical chelating agents include, but are not limited to, sodium edetate citric acid, salts of diethylenetriamine pentaacetic acid, diethylenetriamine pentamethylenephosphonic acid, and stabilizing agents such as sodium edetate and sodium hydrogen sulfite.

Alternative Embodiments

In one embodiment, the formulation further comprises an active agent selected from the group consisting of antioxidants, metal complexes, anti-inflammatory agents, antibiotics, and antihistamines. In one embodiment, the antioxidant is vitamin A, vitamin C, vitamin E, lycopene, selenium, α-lipoic acid, coenzyme Q, glutathione, carotenoid, or Ginkgo biloba. In one embodiment, the formulation comprises acecridine, acetazolamide, anecoltab, apraclonidine, atropine, azapentacene, azelastine, bacitracin, befnolol, betamethasone, betaxolol, bimatoprost, brimonidine, brinzolamide, carbachol, carteolol, celecoxib, celecoxib, Ramphenicol, chlortetracycline, ciprofloxane, cromoglycate, cromolyn, cyclopentrate, cyclosporine, dapiprazole, dexamethasone, dexamethasone, diclofenac, dichlorfenamide, dipivefrin, dorzolamide, ecothiofete, emedastine, epinastine, epinephrine, erynemycin Etoxzolamide, eucatropine, fludrocortisone, fluoro Thorone, flurbiprofen, fomivirzen, flamycetin, ganciclovir, gatifloxacin, gentamicin, homatropine, hydrocortisone, idoxuridine, indomethacin, isoflurofeto, ketorolac, ketotifen, latanoprost, levobetaxolol, levobunocin, levofloxacin, Rhodoxamide, loteprednol, medlizone, metazolamide, metipranolol, moxifloxacin, nafazoline, natamycin, nedocromil, neomycin, norfloxacin, ofloxacin, olopatadine, oxymetazoline, pemirolast, pegaptanib, phenylephrine, physostigmine, pizostigmine Polymyxin B, prednisolone, pu Paracaine, ranibizumab, rimexolone, scopolamine, sezolamide, squalamine, sulfacetamide, suprofen, tetracaine, tetracycline, tetrahydrozoline, tetrizoline, timolol, tobramycin, travoprost, triamcinolone, trifluorometazolamide, trifluridine, trimethoprimum and an active agent selected from the group consisting of: xylometazoline, pharmaceutically acceptable salts thereof, and combinations thereof.

Prophylactic and therapeutic use of zinc compound and antihistamine formulation is detailed below.

The zinc compound and antihistamine formulation described herein are useful for the prevention or treatment of eye diseases. In particular, the present disclosure provides both prophylactic and therapeutic methods for treating subjects at risk for (or susceptible to) eye diseases and medical conditions. Therefore, the present method provides for the prevention and/or treatment of ophthalmic disease in a subject by administering an effective amount of a zinc compound and antihistamine formulation to a subject in need thereof. For example, a zinc compound and antihistamine formulation can be administered to a subject for the purpose of improving one or more factors that contribute to an eye disease or condition.

One aspect of the present technology includes a method of reducing eye disease in a subject for therapeutic purposes. For therapeutic use, the composition or drug treats a symptom of the disease, including a complication and a medium-term pathological phenotype in the progression of the disease, in a subject suspected or already suffering from the disease. Or is administered in an amount sufficient to at least partially inhibit progression. As such, the present disclosure provides a method of treating an individual suffering from an eye disease. In some embodiments, the technique involves diabetic retinopathy, cataract, retinitis pigmentosa, glaucoma, choroidal neovascularization, retinal degeneration, and oxygen induction in a mammal by administering a zinc compound and antihistamine formulation. Methods of treating or preventing certain eye diseases such as retinopathy of reproductivity are provided.

In one embodiment, a zinc compound and antihistamine formulation is administered to a subject to treat or prevent diabetic retinopathy. Diabetic retinopathy is characterized by capillary aneurysms and punctate bleeding. Thereafter, cotton-like vitiligo is formed in the retina due to occlusion of microvessels. Furthermore, due to increased vascular permeability, retinal edema and/or hard vitiligo may form in individuals suffering from diabetic retinopathy. Later, angiogenesis appears and retinal detachment is caused by friction of connective tissue growth in the vitreous. There may also be iris rubeosis and neovascular glaucoma that can turn around and lead to blindness. Symptoms of diabetic retinopathy include poor reading ability, blurred vision, sudden blindness in one eye, a ring around the light, dark spots, and/or flashing light. It is not limited to this.

In one embodiment, a zinc compound and antihistamine formulation is administered to a subject to treat or prevent cataracts. Cataract is a congenital or acquired disease characterized by a decrease in the transparency of the natural lens. An individual suffering from cataract may exhibit one or more symptoms including, but not limited to, clouding of the lens surface, clouding of the lens, and/or swelling of the lens. Typical examples of congenital cataract-related diseases are pseudocataract, intramembranous cataract, coronary cataract, layered cataract, punctate cataract, and filamentous cataract. Typical examples of acquired cataract-related diseases are senile cataract, secondary cataract, brown cataract, concurrent cataract, diabetic cataract, and traumatic cataract. Acquired cataracts are also induced by electric shock, radiation, ultrasound, drugs, systemic diseases, and nutritional disorders. Acquired cataracts further include postoperative cataracts.

In one embodiment, a zinc compound and antihistamine formulation is administered to a subject to treat or prevent retinitis pigmentosa. Retinitis pigmentosa is a disease characterized by damage to rod cells and/or cone cells. Dark lines in the retina are typical in individuals with retinitis pigmentosa. Individuals with retinitis pigmentosa also exhibit a variety of symptoms including, but not limited to, headache, limb numbness or stinging, flashing, and/or visual impairment. See, for example, the following references: Heckenlively et al., Clinical findings and common symptoms in retinitis pigmentosa. Am J Ophthalmol. 105 (5): 504-511 (1988).

Subject to treat or prevent glaucoma. Glaucoma is a genetic disease characterized by increased intraocular pressure, leading to decreased visual acuity. Glaucoma can arise from a variety of ophthalmic conditions that already exist in an individual, such as trauma, surgery, and other structural malformations. Glaucoma can occur at any age but often occurs in older individuals, leading to blindness. Glaucoma patients typically have an intraocular pressure of 21 mmHg or higher. However, normal-pressure glaucoma in which glaucomatous deformation is observed in the visual field and the optic nerve head can occur even if the intraocular pressure is not increased, that is, 21 mmHg or more. Symptoms of glaucoma include, but are not limited to, blurred vision, severe pain in the eyes, headache, visible light around the light, nausea, and/or vomiting.

In one embodiment, a zinc compound and antihistamine formulation is administered to a subject to treat or prevent macular degeneration. Macular degeneration is a disease that typically accompanies aging. The general classification of macular degeneration includes wetness, dryness, and macular degeneration that is not associated with aging. Dry macular degeneration, which accounts for about 80-90 percent of all cases, is also known as atrophic, non-exudative, or dorsenoid macular degeneration. In dry macular degeneration, drusen typically accumulates under the retinal pigment epithelium. If drusen interferes with the function of the photoreceptors in the macula, then blindness occurs. Symptoms of dry macular degeneration include, but are not limited to, astigmatism, central vision distortion, light and dark distortion, and/or color vision changes. Dry macular degeneration may cause a gradual loss of vision.

Wet macular degeneration is also known as angiogenesis, subretinal neovascularization, exudation, or discoid degeneration. In wet macular degeneration, blood vessels grow abnormally under the macula. Blood leaks from blood vessels to the macula, damaging photoreceptors. Wet macular degeneration progresses rapidly and can cause major damage to the central vision. Wet and dry macular degeneration have the same symptoms. However, macular degeneration that is not associated with aging is rare and may be related to heredity, diabetes, malnutrition, injury, infection, or other factors. Symptoms of macular degeneration that do not accompany aging include, but are not limited to, astigmatism, central vision distortion, light and dark distortion, and/or color vision changes.

In one embodiment, a zinc compound and antihistamine formulation is administered to a subject to treat or prevent choroidal neovascularization. Choroidal neovascularization (CNV) is a disease characterized by the growth of new blood vessels in the choroid layer of the eye. Newly formed blood vessels grow on the choroid through Bruch's membrane and enter the subretinal space. CNV can lead to visual impairment and complete blindness. Symptoms of CNV include, but are not limited to, flickering in the affected eye, blinking light, or gray spots, blurred vision, astigmatism, and/or blindness.

In one embodiment, a zinc compound and antihistamine formulation is administered to a subject to treat or prevent retinal degeneration. Retinal degeneration is a genetic disorder associated with the destruction of the retina. Retinal tissue can degenerate for a variety of reasons, including arterial and venous occlusion, diabetic retinopathy, retinopathy of prematurity, and/or posterior lens fibroproliferation. Retinal degeneration generally includes retinal segregation and lattice-like degeneration, and is associated with progressive macular degeneration. Symptoms of retinal degeneration include, but are not limited to, vision loss, blindness, night blindness, visual field stenosis, loss of peripheral vision, retinal detachment, and/or photosensitivity.

In one embodiment, a zinc compound and antihistamine formulation is administered to a subject to treat or prevent oxygen-induced retinopathy. Oxygen-induced retinopathy (OIR) is a disease characterized by microvascular degeneration. OIR is an established model for studying retinopathy of prematurity. OIR is associated with vascular cell damage leading to abnormal angiogenesis. Microvascular degeneration leads to ischemia that contributes to the physical changes associated with OIR. Oxidative stress also plays an important role in OIR vascular occlusion where endothelial cells are prone to peroxidative injury. However, pericytes, smooth muscle cells, and perivascular astrocytes are generally resistant to peroxidative injury. See, for example, the following reference: Beauchamp et al., Role of thromboxane in retina microvascular degeneration in oxygen-induced retinopathy, J Appl Physiol. 90: 2279-2288 (2001). OIR, including retinopathy of prematurity, is generally asymptomatic. However, abnormal eye movements, esotropia, severe myopia, and/or white pupils can be a sign of OIR or retinopathy of prematurity.

In one aspect, the present invention provides a method for preventing eye disease in a subject by administering to the subject a zinc compound and antihistamine formulation that modulates one or more signs or markers of eye disease. A subject at risk for eye disease can be identified, for example, by any or a combination of diagnostic analysis or prognostic analysis as described herein. For prophylactic use, a zinc compound and antihistamine formulation drug is applied to a subject suspected or at risk for a disease or condition, biochemical, histological and/or behavioral symptoms of the disease, or a combination thereof. Administered in an amount sufficient to eliminate or reduce the risk of the disease, reduce the severity, or delay the development, including the disease and the metastatic pathologic phenotype in the progression of the disease. Administration of the prophylactic aromatic cation drug can occur before the onset of an abnormal symptom characteristic so that the disease or injury is prevented or its progression is delayed. Depending on the type of abnormality, for example, a zinc compound and antihistamine formulation that acts to enhance or improve mitochondrial function or reduce oxidative damage can be used for subject treatment. Suitable compounds can be determined based on screening tests described herein.

Measurement of biological effects of treatments based on zinc compound and antihistamine formulation. In various embodiments, appropriate in vitro or in vivo tests are conducted to determine the effectiveness of a particular zinc compound and antihistamine formulation-based therapy and whether its administration is performed as a therapy. In various embodiments, typical cells of a type related to the disorder of the subject are used to determine whether a therapy based on a particular zinc compound and antihistamine formulation has the desired effect on the cell type. In vitro tests can be performed. The therapeutic compound can be tested in a suitable animal model system such as rat, mouse, chicken, cow, monkey, rabbit, etc. prior to testing in human subjects. Similarly, for in vivo testing, any animal model system known in the art can be used prior to administration to a human subject. In one embodiment, administration of a zinc compound and antihistamine formulation to a subject exhibiting symptoms associated with an eye disease results in an improvement in one or more of those symptoms.

The zinc compound and antihistamine formulation is typically formulated to be compatible with its intended route of administration. Examples of routes of administration include parenteral (e.g., intravenous, intradermal, intracavitary, or subcutaneous), oral, inhalation, transdermal (topical), intraocular, iontophoresis, and transmucosal administration.

Solutions or suspensions used for parenteral, intradermal, or subcutaneous administration can contain the following components: water for injection, saline solution, fixed oil, polyethylene glycol, glycerin, propylene glycol, or other syntheses. Aseptic diluents such as solvents; antibacterial agents such as benzyl alcohol or metal parabens; antioxidants such as ascorbic acid or sodium bisulfite; chelating agents such as ethylenediaminetetraacetic acid; acetates, citrates, phosphates, etc. Buffer; and tonicity adjusting agents such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic. For the convenience of the patient or treating physician, the dosage formulation may be provided in a kit containing all the necessary equipment for the therapeutic unit (e.g., drug vials, diluent vials, syringes, and needles).

Examples

The previous examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of treating cataract condition, comprising: delivering therapeutically effective concentrations of a zinc compound and at least one antihistamine for the treatment of an eye condition, wherein the antihistamine is Chlorpheniramine Maleate.

2. The method of claim 1, wherein the zinc compound is zinc sulfate at a concentration of about 0.30% in a buffered solution.

3. The method of claim 2, Chlorpheniramine Maleate at a concentration of about 0.06% in a buffered.

4. The method of claim 2, wherein the delivering therapeutically effective concentrations comprises a treatment time from about 7 days to about 60 days.

5. The method of claim 2, wherein the delivering therapeutically effective concentrations comprises an effective treatment duration is between about 2 and about 60 days.

6. The method of claim 2, wherein the subject's cataract condition improved after 1 week of delivering therapeutically effective concentrations.

7. A method of treating posterior capsular opacification, comprising: delivering therapeutically effective concentrations of a zinc compound and at least one antihistamine for the treatment of an eye condition, wherein the antihistamine is Chlorpheniramine Maleate, and delivering therapeutically effective concentrations address surgical complications/side effects.

8. A method of treating blindness, comprising: delivering therapeutically effective concentrations of a zinc compound and at least one antihistamine for the treatment of an eye condition, wherein the antihistamine is Chlorpheniramine Maleate, and delivering therapeutically effective concentrations to restore vision.

9. A method of treating glaucoma, comprising: delivering therapeutically effective concentrations of a zinc compound and at least one antihistamine for the treatment of an eye condition, wherein the antihistamine is Chlorpheniramine Maleate, and delivering therapeutically effective concentrations to reduce eye pressure to treat acute and chronic glaucoma.

10. The method of claim 1, further comprising treating an eye condition selected from the group consisting of: Cloudy/Blurred Vision, Floaters, Edema, Retinal Hemorrhage, Optic Neuritis, Conjunctivitis, Lacrimation, Retinal Detachment, and Pus.

11. The method of claim 7, wherein the delivering therapeutically effective concentrations comprises an effective treatment duration is between about 2 and about 60 days.

12. The method of claim 8, wherein the delivering therapeutically effective concentrations comprises an effective treatment duration is between about 2 and about 60 days.

13. The method of claim 9, wherein the delivering therapeutically effective concentrations comprises an effective treatment duration is between about 2 and about 60 days.

14. The method of claim 10, wherein the delivering therapeutically effective concentrations comprises an effective treatment duration is between about 2 and about 60 days.

* * * * *